(12) United States Patent
Weisshaupt et al.

(10) Patent No.: US 10,427,841 B2
(45) Date of Patent: Oct. 1, 2019

(54) CENTERING AID FOR CONTAINER LID

(71) Applicant: AESCULAP AG, Tuttlingen (DE)

(72) Inventors: Dieter Weisshaupt, Immendingen (DE); Stefan Schuster, Villingen-Schwenningen (DE); Matthias Schweizer, Tuttlingen (DE); John Gray-Dreizler, Rottweil (DE); Gerold Zieris, Muhlheim (DE)

(73) Assignee: Aesculap AG (DE)

( * ) Notice: Subject to any disclaimer, the term of this patent is extended or adjusted under 35 U.S.C. 154(b) by 0 days.

(21) Appl. No.: 14/423,035

(22) PCT Filed: Jul. 26, 2013

(86) PCT No.: PCT/EP2013/065851
§ 371 (c)(1),
(2) Date: Feb. 20, 2015

(87) PCT Pub. No.: WO2014/029587
PCT Pub. Date: Feb. 27, 2014

(65) Prior Publication Data
US 2015/0225136 A1 Aug. 13, 2015

(30) Foreign Application Priority Data
Aug. 24, 2012 (DE) .................. 10 2012 215 121

(51) Int. Cl.
*B65D 43/08* (2006.01)
*B65D 53/02* (2006.01)
(Continued)

(52) U.S. Cl.
CPC ............ *B65D 43/0204* (2013.01); *A61L 2/26* (2013.01); *B65D 43/0222* (2013.01);
(Continued)

(58) Field of Classification Search
CPC ........ B65D 42/0204; B65D 2543/0204; B65D 2543/00277; B65D 2543/00296;
(Continued)

(56) References Cited

U.S. PATENT DOCUMENTS 3,688,942 A * 9/1972 Mitchell ............ B65D 21/0219
220/324
4,830,182 A * 5/1989 Nakazato ............... B65D 53/02
206/454
(Continued)

FOREIGN PATENT DOCUMENTS

DE 10159382 A1 6/2003
DE 102 30 519 A1 1/2004
(Continued)

OTHER PUBLICATIONS

International Search Report for PCT/EP2013/065851 dated Oct. 11, 2013.

*Primary Examiner* — J. Gregory Pickett
*Assistant Examiner* — Niki M Eloshway
(74) *Attorney, Agent, or Firm* — RatnerPrestia

(57) ABSTRACT

The present application discloses a centering aid for a container having a container trough, with an access opening, a container lid and a seal. In the closed state of the container, the seal is arranged between the container trough and the container lid. The centering aid has a first centering device, which is provided on either the container lid or the container trough, and a second centering device, which is provided on the other of either the container lid or the container trough. The first and second centering devices interact in such a way as to ensure that, in the closed state of the container, the seal is in contact with the container trough and with the container lid along the entire periphery of the access opening.

15 Claims, 5 Drawing Sheets

(51) Int. Cl.
- *B65D 43/02* (2006.01)
- *A61L 2/26* (2006.01)
- *B65D 45/20* (2006.01)
- *B65D 45/18* (2006.01)

(52) U.S. Cl.
CPC ........ *B65D 45/20* (2013.01); *A61L 2202/182* (2013.01); *B65D 2251/04* (2013.01); *B65D 2255/06* (2013.01); *B65D 2543/0099* (2013.01); *B65D 2543/00194* (2013.01); *B65D 2543/00277* (2013.01); *B65D 2543/00296* (2013.01); *B65D 2543/00564* (2013.01)

(58) Field of Classification Search
CPC ........... B65D 2543/00453; B65D 2543/00972; B65D 43/0204; B65D 43/0222; B65D 45/20; B65D 2251/04; B65D 2255/06; B65D 2543/00194; B65D 2543/2543; B65D 2543/00564; B65D 2543/0099; A61L 2/26; A61L 2202/182
USPC ................ 220/795, 324, 849, 797, 803, 804
See application file for complete search history.

(56) References Cited

U.S. PATENT DOCUMENTS

| | | | |
|---|---|---|---|
| 5,046,632 A | | 9/1991 | Bordner |
| 5,377,861 A | * | 1/1995 | Landis ............... B65D 43/0212 206/508 |
| 5,887,744 A | * | 3/1999 | Mejias ................ B65D 50/067 220/284 |
| 6,010,670 A | | 1/2000 | Berry, Jr. |
| 6,276,552 B1 | * | 8/2001 | Vervisch ................ F16K 35/10 220/315 |
| 6,789,692 B2 | * | 9/2004 | Prezelin ................ B65D 51/16 190/119 |
| 6,845,877 B2 | * | 1/2005 | Diesterbeck ....... B65D 21/0219 206/508 |
| 7,021,485 B1 | | 4/2006 | Baker et al. |
| 8,308,010 B2 | * | 11/2012 | Letica ................ B65D 43/0279 215/216 |
| 8,627,972 B2 | * | 1/2014 | Thomas ................. A61B 19/02 206/349 |
| 2012/0234850 A1 | * | 9/2012 | Picard ................. B65D 43/162 220/833 |

FOREIGN PATENT DOCUMENTS

| | | |
|---|---|---|
| DE | 20 2012 100 997 U1 | 5/2012 |
| EP | 2 404 567 A1 | 1/2012 |
| EP | 2 478 921 A1 | 7/2012 |
| JP | 57117297 A | 7/1982 |
| JP | 2001354281 A | 12/2001 |
| JP | 2006176160 A | 7/2003 |
| JP | 2007145424 A | 6/2007 |

* cited by examiner

CENTERING AID FOR CONTAINER LID

The present invention relates to a centering aid for a container lid and, in particular a centering aid for a lid of a medical sterilization container.

Particularly in sterilization containers, but also in many other containers, a seal is provided between the container lid and the container trough. The seal between the container lid and the container trough can, for example, be a double seal which is designed in the form of a hinged seal. Two sealing areas are provided in this type of seal. A first sealing section is formed by placing a first sealing lip of the seal mounted on the container lid on to the front face of the wall of the container trough. In so doing, the first sealing lip is deformed upwards with respect to its mounting position thereby pushing a second sealing lip, which is arranged below the first sealing lip, inwards so that it laterally engages with the outside of the wall of the container vessel forming a second sealing section. Depending on the dimensioning of the sealing lips, of the container lid and of the vessel trough, a certain lateral clearance is provided with which the container lid can be placed on the container trough. Lateral clearance here means clearance in any direction within the sealing plane. The sealing plane is defined by the course of the seal along the access opening of the container trough. If the seal does not run along one plane, the sealing plane is a normal plane to the vector of the access opening of the container trough.

However, if the container lid is placed at an angle or offset on the container trough, it may be that on one side of the container the second sealing lip is partially placed on the front face of the wall of the container trough so that the above functional principle is no longer effective. At the same time, it may happen that on the opposite container side the first sealing lip is at least partially positioned adjacent to the wall of the container trough so that no sealing section at all is formed between the container lid and container trough at this point and air can flow freely through the gap formed inside and outside the container.

A similar thing can happen if a simple seal is arranged between the container lid and the container trough. Silicone is often used as the material for this type of seal as it has good elastic properties and, inter alia, can survive a sterilization process without damage. However, as silicone seals are usually very soft, they do not provide the user of the container with distinct haptic feedback as to whether the container lid is correctly positioned on the container trough. In addition, as a result of its softness the seal itself is little suited to correctly aligning the container lid with the container trough. However, the seal can also be made from other elastomers.

It is, therefore, an object of the present invention to provide a centering aid and/or a positioning aid for a container which ensures that the container lid is placed in a correct location and/or position on the container trough thereby assuring the sealing of the inside of the container from the outside. Sealing here means not only a total seal which does not allow any mediums to be exchanged between the inside of the container and the outside, but it also means, for example, a seal by which it is ensured that an exchange of mediums can only occur through a membrane provided on a container so that no unsterile medium can enter the inside of the container as is often the case with medical sterilization containers.

The object of the present invention is solved by means of a centering aid according to claim 1. Further advantageous arrangements of the centering aid are the subject matter of the dependent claims.

In accordance with one aspect of the present invention a centering aid is prepared for a container having a container trough with an access opening, a container lid and a seal which is arranged between the container trough and the container lid in the closed state of the container. The centering aid has a first centering device which is provided either on the container lid or on the container trough, and a second centering device which is provided on the other of either the container lid or the container trough. In so doing, the first and second centering devices interact in such a way as to ensure that, in the closed state of the container, the seal is in contact with the container trough and with the container lid along the entire periphery of the access opening.

The access opening is thereby the opening through which the objects can be introduced into or taken out of the container and, in the case of a container, is usually on the top of the container trough. The seal is usually of annular design and is attached either on the container trough or on the container lid. In the case of medical sterilization containers it can happen that the seal is affixed detachably to the container lid. It is also possible that the seal is attached neither to the container trough nor to the container lid, however the handling of the container during opening and closing is significantly faster and easier if the seal is not arranged detachably between the two container components. However, more frequently the seal is stuck to one of the container components, preferably stuck in the container lid, or is injection molded directly on to one of the container components. All this can, of course, be implemented in containers other than medical sterilization containers as well.

The object of the seal is to prevent a medium—usually air—from flowing between the edge of the container trough and the container lid. The seal is to securely separate the inside of the container from the outside of the container. This is the case with medical sterilization containers to prevent unsterile air or other unsterile media from entering the inside of the container and, therefore, keep the instruments and other objects in the container safely sterile. A sterile exchange of media and pressure compensation can be ensured in this case, for example, via a filter membrane or other filtering devices.

In the closed state of the container, the container lid rests on the seal which, in turn, rests on the container trough. In so doing the seal usually rests on the front face of the wall of the container trough. In an arrangement such as this where the seal is between the container trough and container lid the aim primarily is to prevent a horizontal displacement or horizontal offset of the container lid in relation to the seal and/or of the seal. If the seal is attached either to the container lid or to the container trough only the horizontal offset between the seal and the respective other container component must be ensured. The container lid can be prevented from lifting off from the seal and/or the seal can be prevented from lifting off from the container trough by having the container lid fixed and/or harnessed towards the container trough, for example, by a fastener with fastening clips By means of a construction of this kind it is ensured that the seal performs its sealing function between the container lid and the container trough as the two components cannot be displaced so far from one another in a horizontal direction that a gap is created between the seal and one of the container components.

In accordance with an advantageous arrangement of the present invention, with the centering aid in the closed state of the container the clearance between the first and the second centering device is smaller than the clearance between the container lid and the container trough. The clearance between the container lid and the container trough is meant here in the case where no centering aid is provided. In the case of a container with a centering aid the centering aid bounds the clearance between the container lid and the container trough which only functions if the clearance between the first and the second centering aid is smaller than between a corresponding container lid and a container trough without a centering aid.

The clearance between the container lid and the container trough depends significantly on the material and the form of the seal, as well as on the geometry of the container lid and of the edge of the container trough upon which the container lid is placed. For the most part, the seal is made from very elastic and flexible material and has a specific width so that the container lid can be quickly and easily placed on the container trough without the user paying too much attention thereto. The seal is deformed if the container lid is placed askew on the container trough and it does not assist in centering the container lid on the container trough. The geometry of the container lid and of the container trough should also facilitate a quick simple and secure closing of the container.

According to a further advantageous arrangement of the present invention, the first centering device has a number of male centering elements and the second centering device has a number of female centering elements. The centering of the container lid in relation to the container trough is thereby achieved in that the male centering elements penetrate the female centering elements and are accommodated by them or, however, is achieved thereby in that the male centering elements come into contact with the female centering elements. In so doing the male centering elements extend at least proportionately towards the female centering elements of the respective other centering device.

According to another advantageous arrangement of the present invention the first and second centering devices each have at least one male and one female centering element. By means of such an arrangement male and female centering elements can each be provided on container lid and container trough.

According to another advantageous arrangement of the present invention at least one male centering element is fundamentally in the shape of a parallelepiped—in particular of a cuboid—, of a pyramid, of a truncated pyramid, of a prism, of a cylinder, of a cone, or of a partial ellipsoid. Or at least one male centering element is made from several similar and/or different examples of the above mentioned bodies. The associated female centering element preferably has a corresponding negative shape so that the male centering element is fundamentally accommodated to interlock by the female centering element. As an alternative the female centering element can, however, have a different shape and, therefore, the centering and/or positioning of both centering devices towards each other is not achieved via the entire axial length of the male and female centering element but rather via specific sections of said length. One example of this is a conical male centering element which is accommodated in a cylindrical female centering element whereby the radii of the circular base areas of both centering elements are fundamentally identical. With a constellation such as this, an interlocking between the two centering elements in a transverse direction to the axis of the centering elements only occurs in the area of the foot of the conical male centering element. Otherwise a gap and/or cavity is formed between the two centering elements.

According to a further advantageous arrangement of the present invention at least one male centering element and/or one female centering element has an at least partially conical area so that the clearance between the male and the female centering element at the beginning of the movement to place the container lid is larger than in the closed state of the container. In so doing the associated female centering element and/or male centering element preferably has a corresponding negative and/or positive shape. With a construction such as this, the container lid need only be centered very loosely in relation to the container trough when being placed in order to achieve a first—initially very loose—meshing of the male and associated female centering elements. If the container lid is then placed further on to the container trough, the cross section of the male and female centering elements in the conical area converges either intermittently or continuously. The shape of the two centering elements, therefore, corresponds advantageously so that dirt cannot collect in the otherwise created cavity. In the case of medical sterilization containers, the formation of cavities between the centering elements could lead to dirt collecting in the cavities and possibly falling into the container upon opening and contaminating the instruments and object contained therein, at least on the face of it. Although the dirt itself would have been sterilized in the process, it is not possible to tell that by looking at the dirt. In addition, the dirt is presumably only noticed when it is in the container trough which creates the impression that the instruments and objects were not properly cleaned prior to sterilization. This problem can be remedied either by not creating any cavities between the centering elements, or by connecting such cavities via a rinsing opening to the outside so that any dirt present can be flushed out. In the event that no cavity is created between the male and female centering elements, the dirt that has collected in a female centering element, prevents the male centering element from being fully accommodated in the female centering element and, therefore, also prevents the container lid from being placed completely on the container trough and prevents the container from being closed. This shows the user that there must be contamination in at least one centering element so that he has the opportunity to remove this contamination before the container is closed. In this way contamination in a medical sterilization container is identified and removed prior to the cleaning and sterilization of the container whereby it cannot happen that dirt can emerge and possibly fall into the container when the container is opened.

According to yet another advantageous arrangement of the present invention the centering devices are arranged such that they are arranged outside the inside of the container in the closed state of the container. In this way the usable space inside the container is not reduced in size by the centering device.

In addition, in this way it is possible to carry out a better visual check of whether the container lid has been correctly placed on the container trough, even when completely closed.

According to one more advantageous arrangement of the present invention the first centering device is provided directly, or via a front panel arranged on the external front faces of the container trough, on the external front faces, and/or the second centering device is provided in the surrounding of fastening elements which are provided on at least two opposite sides of the container lid. In the case of the formation described first, the first centering device need not be formed directly on or with the container trough, but rather can be formed on or with the front panel or with parts of said panel and then mounted on the container trough. An additional component, on which the first centering device is provided, can also be arranged between a front face of the container and a front panel. This component can, for example, be a base plate which is permanently connected to the front face and provides a mounting surface for the front panel. In this way easier mounting and a larger selection of materials are ensured for the first centering device. The two front faces are relatively far apart from one another (in relation to the dimensions of the container), so that overall the centering device extends across a large area of the container and, therefore, as a result of the clearance, even if small, between the centering devices it permits a lesser rotation of the container lid in relation to the container trough than if the dimensions of the centering device were only very small. In the case of the formation described second, the second centering device is provided in the surrounding of fastening elements with the assistance of which the container lid is held on the container trough or the container lid is stretched towards the container trough. The user pays more attention to the area of the fastening elements when closing the container as the seal requires this of him. Consequently, he is able to check the correct centering of the container lid on the container trough particularly easily and simply if the second centering device is located in the area of the fastening elements. Furthermore, the second design also allows a container lid with more than two fastening elements to be attached to the container trough and the centering elements to be distributed accordingly. For example, a square container can be provided with one fastening element on each side of the container lid. A male and/or a female centering element is provided on both sides of each fastening element and the container trough has corresponding fastening element mounts and female and/or male centering elements.

According to a special design, the centering aid can also be part of the seal. For example a centering element can be provided on a fastening element which is provided on the container lid and can be pivoted. However, it is also possible that the pivotable fastening element is itself a centering element. In this case the container lid is first place on the container trough. Then the fastening element is swiveled towards the container trough. In so doing the lateral surfaces of the fastening element, which on this occasion represents the male centering element, comes into contact with contact surfaces on the fastening element mount which represent the female centering element. During the pivoting process the contact of the lateral surfaces between the fastening element and fastening element mount is initially produced in the area which is closest to the fastening element and then reproduces itself up to the free end of the fastening element. If the lateral surfaces of the fastening element and fastening element mount are arranged at such an angle to the axis of the fastening element that they converge at the free end of the fastening element, a self-centering of the container lid on the container trough is achieved by this means as well. The self-centering operation can be adjusted by means of a special design of the thickness of the fastening element, or by providing a curve along the length of the fastening element.

According to a further advantageous arrangement of the present invention, the first centering device has four planar projections which run in a lateral direction to form an angle in relation to the longitudinal axis of the container and the transverse axis of the container whereby the projections are provided on both sides of a fastening mount on the top of two front panels which are arranged on both outer front faces of the container trough. In so doing, the planar projections are more strongly beveled on their lateral front face than on their central front face so that the projections fundamentally taper in a distal direction externally. The second centering device also has four recesses which are adjusted appropriately to accommodate and interlock the corresponding planar projections, and two recesses are each formed in a component which is provided between the internal front faces of the container lid and the seal. This design According to yet another advantageous arrangement of the present invention the first centering device is provided on the inside of the container lid inside the seal, and the second centering device is provided on the container trough. By means of this design a centering aid is created which is arranged on the inside of the container The first centering device can then, for example, comprise at least two male centering elements which are arranged on at least two different sides of the container lid inside the seal but near to the edge of the container and extend at least proportionately downwards. The female centering devices thereby comprise oblique contact surfaces which are formed on the inside of the wall of the container trough in the area of the upper edge of the container trough. The oblique contact surfaces are formed in such a way that when looked at from top to bottom they run from the outside inwards. If the male centering elements come into contact with one or more of the female centering elements this contact ensures a self-centering during the course of the closing process until all male centering elements lie flat on the associated female centering elements and the container is closed.

According to a further advantageous arrangement of the present invention the first centering device comprises an even number of male centering elements which are arranged in the corners of the container lid and/or in the middle of each side of the container lid. Particularly advantageous here is the arrangement in the corners as, in this way, the centering elements are spaced to the maximum and the small clearance between male and female centering elements thereby has the smallest impact on the position of the container lid in relation to the container trough.

According to a further advantageous arrangement of the present invention the centering devices are designed from a material that has a higher modulus of elasticity than the seal, preferably from a rigid plastic or metal. In this way good centering can be ensured by means of simple geometric shapes from the male and female centering elements. In particular, aluminum and alloys of aluminum can be considered as the metal and PEEK, for example, as the plastic. Silicone is often used for the seal which has a very low modulus of elasticity so that there are numerous possible materials for the centering elements. However, it is also possible to design the male centering elements from a harder material than that of the female centering elements and to choose both materials based on there being particularly low friction between the male and female centering elements. This increases the comfort in using the container. The male centering elements are more likely to be subjected to an impact load or other inadvertent load than the female centering elements which suggests that these be formed from the more stable material. However, this does not exclude the possibility that the male centering elements be formed from the softer material in order to reduce the risk of the projections, which form the male centering elements, causing injuries as a result, for example, of them failing at predetermined breaking points. In this case the male and/or female centering elements are provided to be interchangeable.

According to a further advantageous arrangement of the present invention the centering aid has a symmetrical construction with an angle of rotation of 360%/n whereby n is a positive integer, preferable an integer greater than one. With this design the principle according to the invention can also be applied comfortably to containers which, for example, have a triangular, square or hexagonal shape. However, this construction also has the advantage for a standard square container of there being not just one position and/or alignment for the container lid in relation to the container trough in which the centering devices can engage with each other, but rather the container lid can be turned by 360%/n and still fit on the container trough. Therefore, for each container lid, there are correct positions and/or alignments relative to the container trough and not just one single position and/or alignment. Accordingly it could be said that in this way the container lid of a square container does not know front or back, instead it fits on the container trough in both directions.

Further advantages and characteristics of the invention are apparent to the person skilled in the art from the attached figures and the detailed descriptions of the exemplary embodiments.

The exemplary embodiments are described in detail below with reference to the figures.

A first exemplary embodiment of the present invention is described in detail below with reference to FIGS. 1 to 13.

Figure 1:
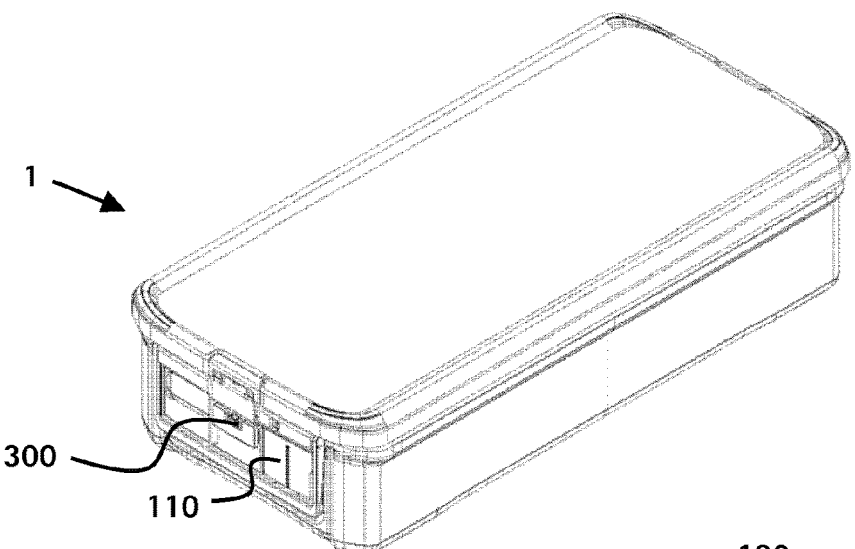
FIG. 1 shows an isometric view of a medical sterilization container having a centering aid according to the first exemplary embodiment.
Figure 2:
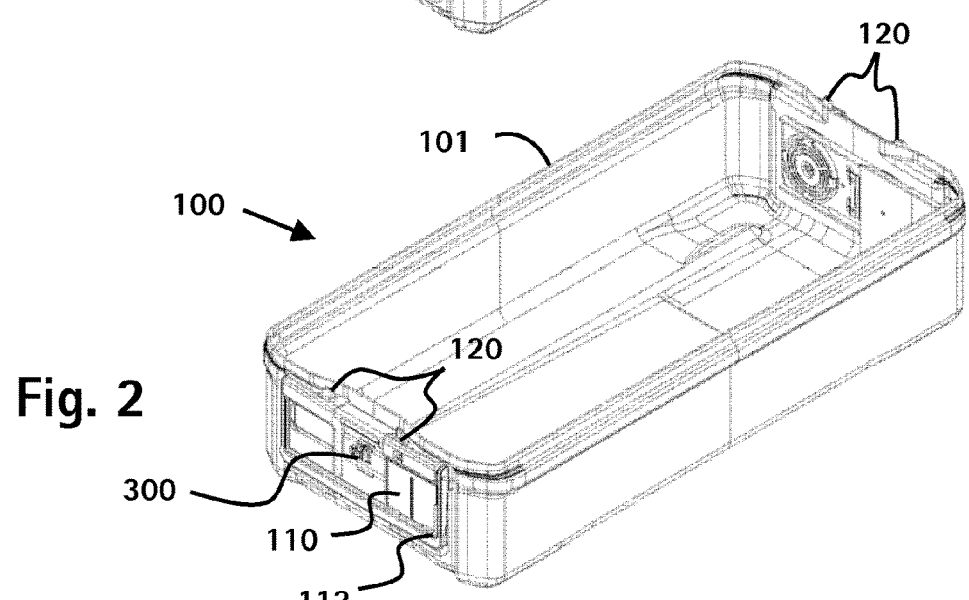
FIG. 2 shows an isometric view of a container trough of the medical sterilization container from FIG. 1.
Figure 3:
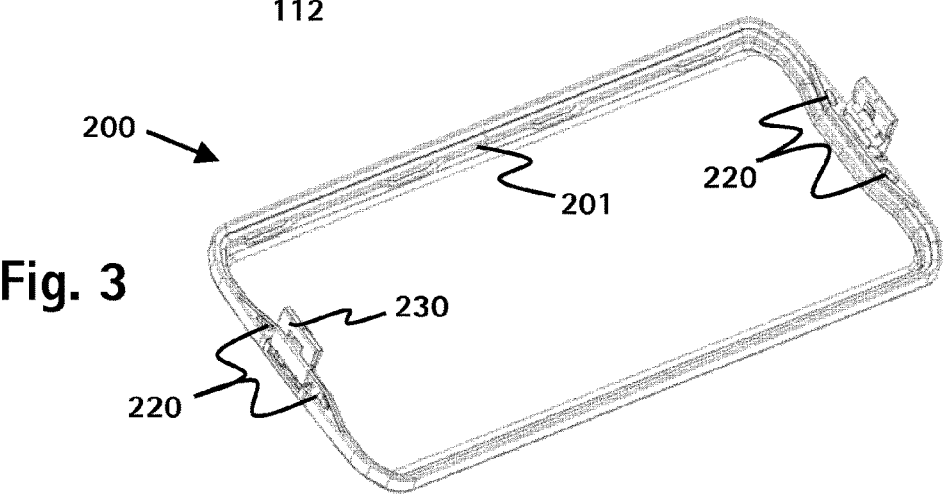
FIG. 3 shows an isometric view of a container lid of the medical sterilization containers from FIG. 1.
Figure 4:
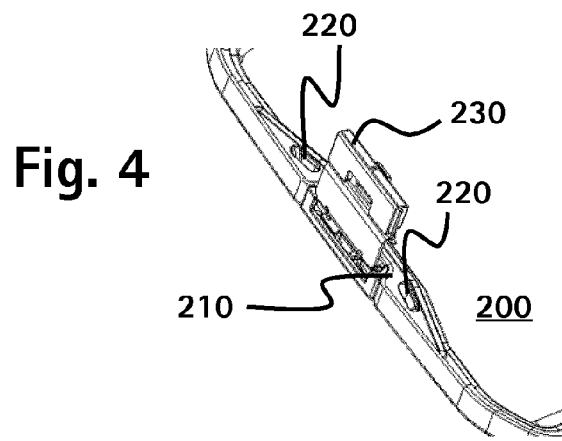
FIG. 4 shows a perspective view of a section from FIG. 3.
Figure 5:
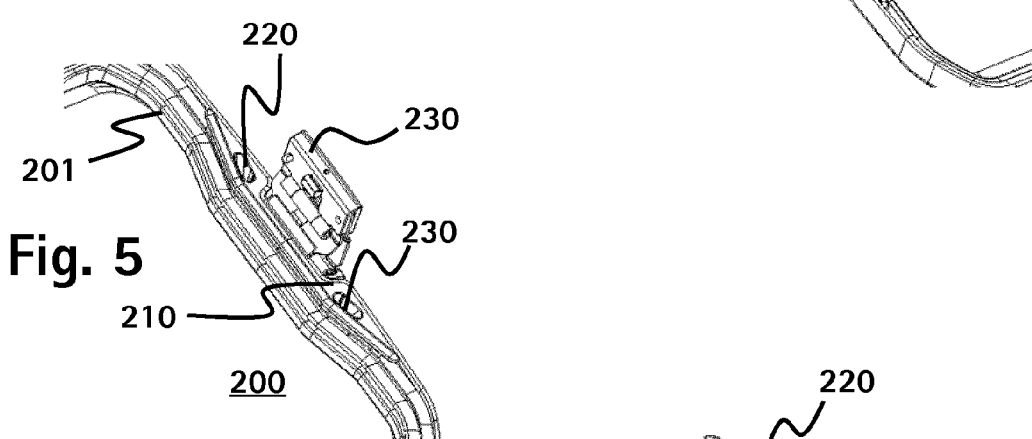
FIG. 5 show a further perspective view of a section from FIG. 3.
Figure 6:
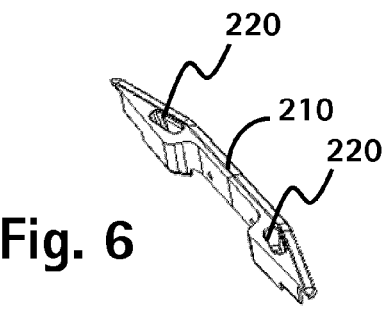
FIG. 6 shows a perspective view of a component with two female centering elements according to a first exemplary embodiment
Figure 7:
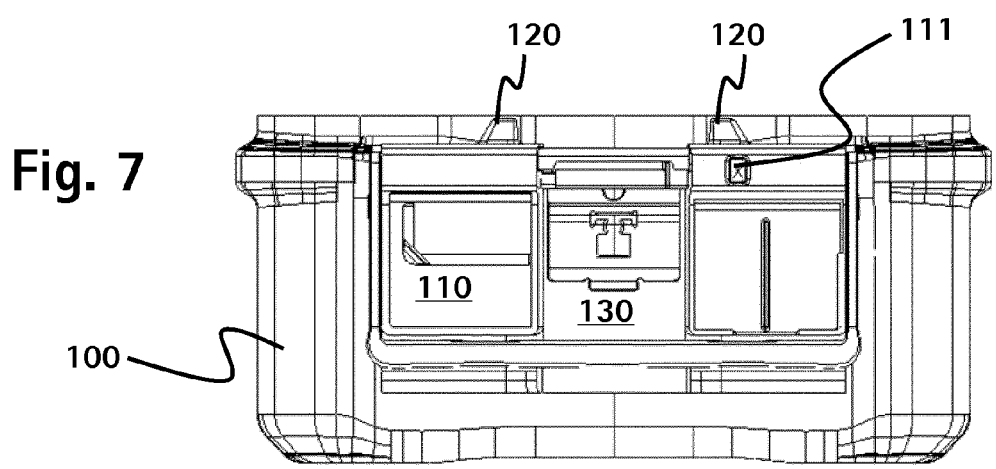
FIG. 7 shows a view of a container trough of the medical sterilization containers from FIG. 2 from the front.
Figure 8:
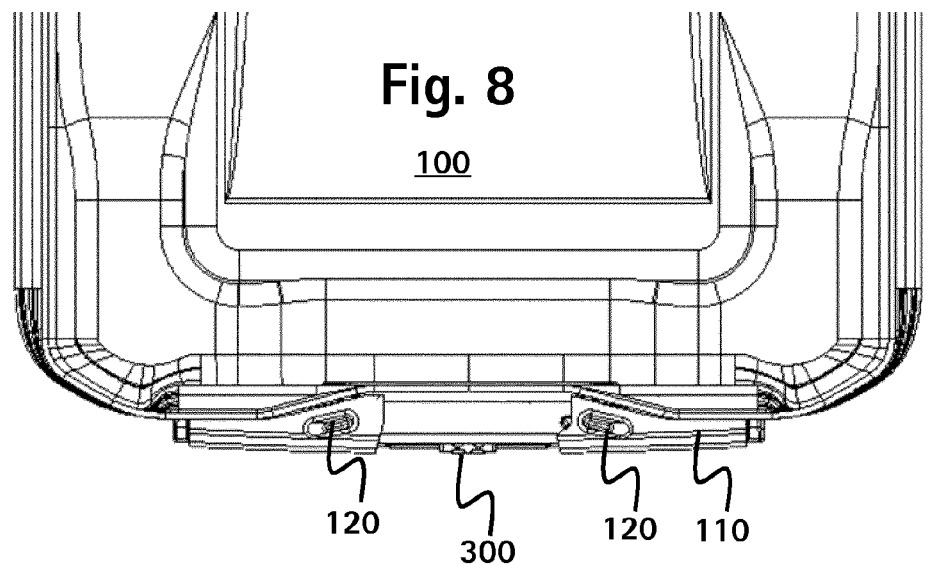
FIG. 8 shows a view of a container trough of the medical sterilization containers from FIG. 2 from the top.
Figure 9:
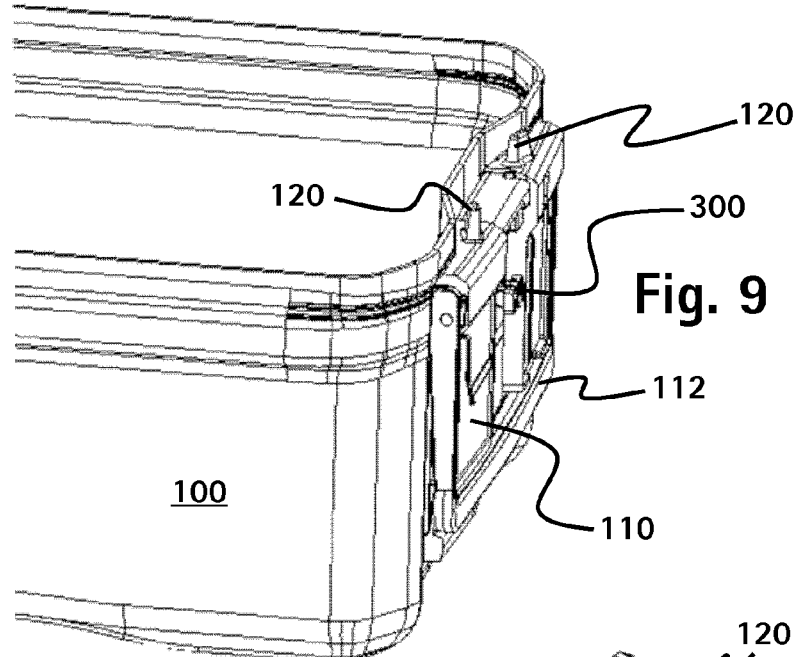
FIG. 9 shows a perspective view of a section of a container trough of the medical sterilization containers from FIG. 2.
Figure 10:
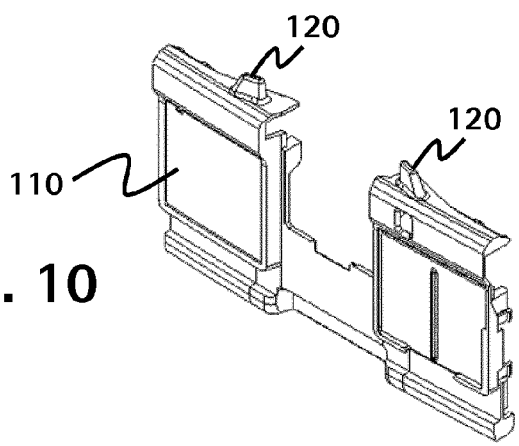
FIG. 10 shows a perspective view of a component having two male centering elements according to a first exemplary embodiment
Figure 11:
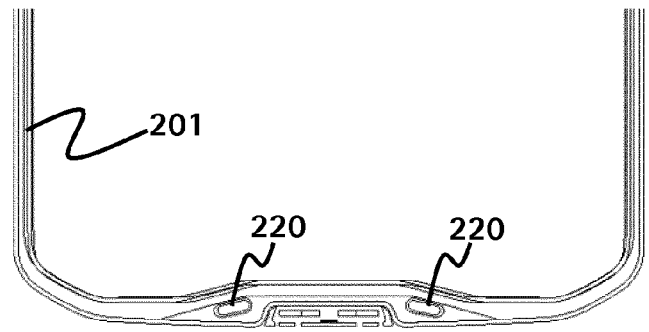
FIG. 11 shows a horizontal cut through the container lid from FIG. 3.

As is shown in FIG. 1, the container 1 from the first exemplary embodiment is a medical sterilization container 1 having a container trough 100 and a container lid 200. The container trough is provided with a front panel 110, a sterile indicator 111 and a handle 112. A front panel 110 is provided on both front faces of the container trough 100 whereby its construction can differ in parts. The container lid 200 has a seal 201 which runs along the edge of the container lid 200, which is stuck to the container lid 200, and which interacts with the edge 101 of the container trough 100 to seal the inside of the container 1 securely. The container lid 200 has two fastening clips 230 which can be pivoted and which can each be introduced into a corresponding sealing mount 130 on the outside front face of container trough 100 and locked to ensure a seal between the container lid 200 and the container trough 100. A security seal 300 can be pushed through fastening clip 230 and anchored in sealing mount 130 to securely demonstrate to the user that the container 1 has not yet been opened following a sterilization operation.

A first centering device comprising male centering elements 120 is provided on the container trough 100 and a second centering device comprising a female centering element 220 is provided on the container trough. The first and second centering devices are appropriately adapted to interact in such a way as to ensure that, in the closed state of the container, the seal 201 is in contact with the container trough, or more specifically with the edge 101 of the container trough 100 and the container lid 200 along the entire periphery of the access opening of the inside of container 1. In this case the first and second centering device interact in such a way that the female centering elements 220 are pushed on to the male centering elements 120. By providing only a certain clearance, which is smaller than the tolerance and/or clearance of the seal 201 in relation to an oblique positioning of the lid in relation to the trough 100, between the male and the female centering elements 120, 200 in the closed state of the container 1, 200 it is thus ensured that the seal 200 tightly seals the container 1. The seal 201 is thereby designed and arranged such that, if no centering device is provided on the container 1, a larger clearance is allowed when positioning the lid 200 in relation to the trough 100 with the sealing effect of the seal 201 being lost. In the above case seal 201 is a double seal with two sealing lips. One sealing lip rests from above on the edge 101 of the container trough 100 whereby a second sealing lip is pushed from outside towards the external wall of the container trough 100. This happens by the first sealing lip being moved upwards which leads to the second sealing lip being rotated inwards. A seal of this type has a very high tolerance to the lid 200 being placed obliquely on the trough 100. It goes without saying that the present invention can also be applied to other containers and vessels which are provided with other seals, for example, with seals with just one sealing lip.

The male centering elements 120 according to this exemplary embodiment comprise a fundamentally planar body. When viewing containers 1 from the front in accordance with FIG. 7 the male centering elements 120 have a steep internal wall and a comparatively flatter external wall so that they form a trapezoidal shape. The two lateral walls of the male centering elements are fundamentally parallel to each other. The female centering elements 220 in accordance with this exemplary embodiment have a shape which corresponds to the shape of the male centering elements 120 and are only a little larger so that the male centering elements 120 can be accommodated in the female centering elements 220 without compulsion.

They have a conical design as a result of the relatively flat ascending external wall and the relatively steeply ascending internal wall of the male centering elements 120. In this way the clearance between a male and a female centering element at the beginning of the movement to place the container lid is larger than in the closed state of the container. The male centering elements 120 and the female centering elements 220 are each arranged outside the interior of the container. The male centering elements 120 are thereby arranged on the front panels 110 which are attached to the external front faces of container trough 100. The female centering elements 220 are provided in pairs on a component 210 which is attached to the container lid 200 in the area of the fastening clips 230 between the seal 201 and the fastening clips 230, i.e. on the front faces of the container lid 200. The upper edge 101 of the container trough 100 defines the access opening in the container 1 and the seal 201 is adapted to the course of the upper edge 101 of the container trough 100.

The first centering device of this exemplary embodiment has, therefore, four planar projections 120, i.e. the four male centering elements 120. As is shown particularly well in FIGS. 8 and 9, these elements occupy an angle in relation to the longitudinal axis and the transverse axis of the container in a lateral direction whereby the male centering elements 120 are provided on both sides of a fastening mount 130 on the top of the two front panels 110 which are arranged on both external front faces of the container trough 100. The male centering elements 120 are more heavily beveled on their lateral front face than on their central front face so that the projections fundamentally taper in a distal direction from the outside as can be easily seen in FIGS. 2, 7, 8 and 12.

In the present exemplary embodiment the male centering elements are made from the same material as front panels 110, i.e. from stainless steel. The female centering elements 220 are designed in the component 210 which, in this exemplary embodiment, is made from plastic, or more specifically from PEEK (polyetheretherketone). In this way, the centering devices are formed from a material that has a higher modulus of elasticity than the seal which, in this case, is made from silicone.

The centering aid according to this exemplary embodiment, comprising four male and four female centering elements 120, 220, has a symmetrical construction with an angle of rotation of 180°. This means that the container lid 200 can be placed in two different positions rotated through 180° on the container trough 100.

Figure 12:
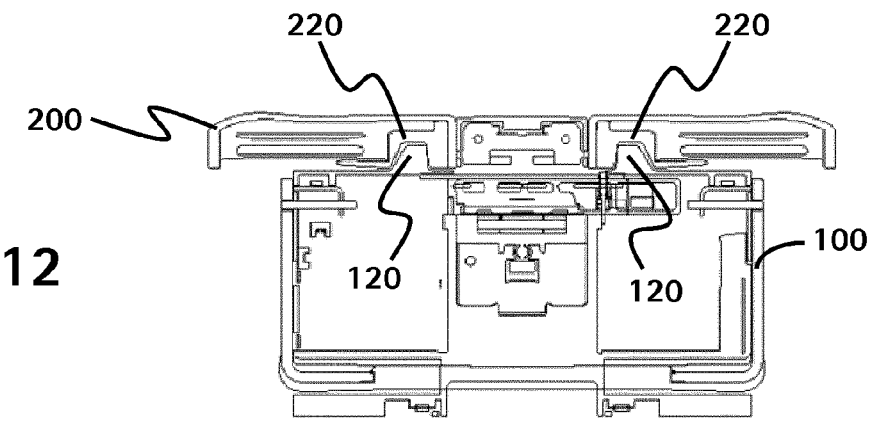
FIG. 12 shows a vertical cut through the container lid and the container trough in accordance with FIG. 1.
Figure 13:
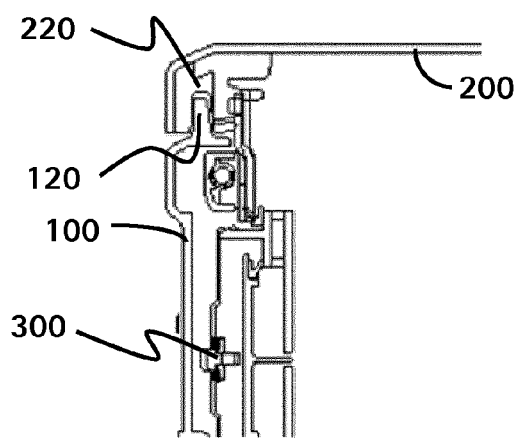
FIG. 13 shows a further vertical cut through the container lid and the container trough in accordance with FIG. 1.

FIGS. 12 and 13 show how the male centering elements 120 are accommodated in the female centering elements 220.

Figure 14:
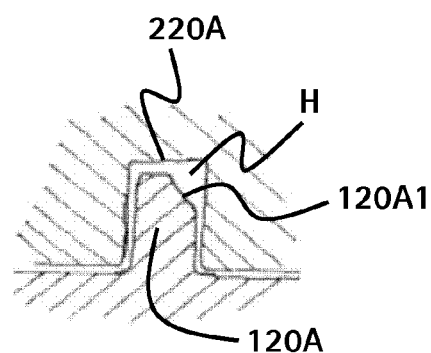
FIG. 14 shows a schematic view of a male and a female centering element according to a second exemplary embodiment.

A second exemplary embodiment of the present invention is describe below with reference to FIG. 14. Only the differences to the first exemplary embodiment are dealt with here as the main part of both exemplary embodiments is identical.

The male centering elements 120A of this exemplary embodiment comprise a cuboid from which a three-sided prism was removed. In this way an oblique surface is created 120A1 which forms a conical part on the male centering element 120A and thereby helps to align the container lid 200 with the container trough 100. The female centering elements 220A are in the shape of a cuboid opening 220A. Therefore, a cavity H is formed between a male centering element 120A and a female entering element 220A. The shape of the male and female centering elements 120A, 220A need not therefore be shaped correspondent.

Moreover, in this exemplary embodiment the male centering elements 120A are provided on the container lid 200 and the female centering elements 220A are provided on the container trough 100. In so doing the centering elements 120A, 220A can be provided directly, or indirectly via further components, on the container trough 100 and the container lid 200. Furthermore, in this exemplary embodiment the container is square. Furthermore, the four fastener straps 230 are provided on the container lid 200 in the middle of each side of the container lid 200. Accordingly the container trough 100 has four locking mounts 110 in the middle on each side of the container trough 1. The front and back of container 1 each have a front panel 110 in which a locking mount 110 is designed. The locking mounts 110 which are provided on both lateral walls of container 1 are formed on additional panels which are attached from the outside to the side walls of the container trough 100. Two female centering elements 220A are designed on each front panel 110 and each side panel. In this exemplary embodiment the container lid 200 is provided with four components 210 whereby in these components 210 the male centering elements 120A are designed. In this way a container lid 200 is produced which can be placed on the container trough 100 in four different positions, i.e. each rotated by 90° in the horizontal. In order to prevent contamination collecting in the cavity H, the cavity H can be connected to the outside via a channel so that any contamination found in the cavity H during a cleaning operation can be flushed out with the rinsing liquid. Alternatively the female centering elements 220A can also be completely open on the side which does not face the male centering elements 110A, i.e. designed as square through-holes here.

Figure 15:
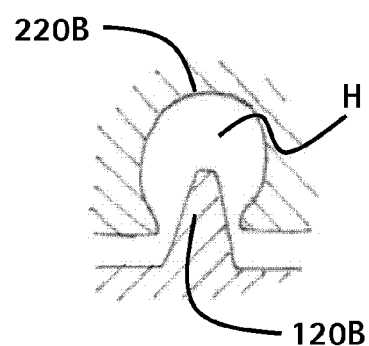
FIG. 15 show a schematic view of a male and a female centering elements according to a third exemplary embodiment.

A third exemplary embodiment of the present invention is described in detail below with reference to FIG. 15 whereby again only the differences to the first exemplary embodiment are described.

In this exemplary embodiment, the male centering elements 120B are formed by means of a slightly truncated cone. Thus the male centering elements 120B in this exemplary embodiment are designed rotationally symmetrical. The female centering elements 220B more or less have the shape of a conical cavity which is open towards the male centering elements 120B. In the case of these centering elements 120B, 220B as well, a cavity FI is formed which alternatively can also be connected to the outside by means of a channel. Furthermore, in this exemplary embodiment, male centering elements 120B and female centering elements 220B are provided in a circumferential direction of the container trough 100 and of the container lid 200 alternately on said trough and said lid whereby a male centering element 120B and a female centering element 220B are always opposite each other. By means of this arrangement of the male and the female centering elements 120B, 220B, the symmetrical construction of the container trough 100 and the container lid 200 is maintained, i.e. the container lid 200 can still be placed in two positions rotated by 180° on the container trough 100.

Figure 16:
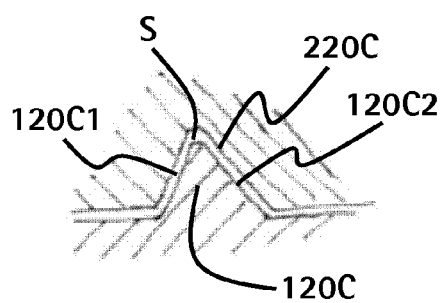
FIG. 16 shows a schematic view of a male and a female centering element according to a fourth exemplary embodiment.
Figure 17:
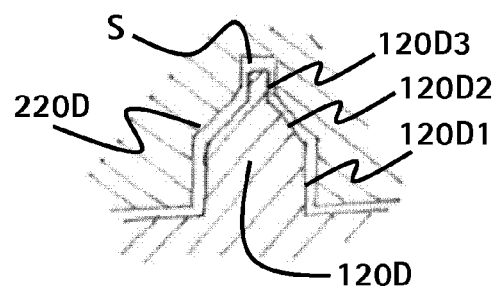
FIG. 17 shows a schematic view of a male and a female centering element according to a fifth exemplary embodiment.

A fourth exemplary embodiment of the present invention is described in detail below with reference to FIG. 16 whereby again only its differences to the first exemplary embodiment are described here. The male centering elements 120C of this exemplary embodiment are formed as four-sided oblique pyramids. FIG. 17 shows a cut through a male and a female centering element 120C, 220C in both principal directions. This means that the male centering element 120C has two steep flanks 120C1 and two flat flanks 120C2. The two steep flanks 120C1 are both arranged towards the center of the container 1 and the two flat flanks are both arranged away from the center of container 1. The female centering elements 220C have a shape corresponding to that of the male centering elements 120C. A channel can be provided in this case as well which connects gap S, which is formed between the male and female centering elements 120C, 220C, to the outside. In this way it can be ensured that no contamination establishes itself in the female centering elements 120C thereby preventing the male centering elements 120C from being able to be introduced correctly into the female centering elements 220C. This type of channel is preferably designed on or in the area of the floor (of the deepest section) of the female centering elements.

It goes without saying that it is possible with this exemplary embodiment, as well as with the other exemplary embodiments, to arrange the steep flanks of the male and female centering elements towards the outside. Care should preferably be taken to ensure that the centering elements are provided symmetrically.

A fifth exemplary embodiment of the present invention is described below with reference to FIG. 17. Subsequently again only the differences to the first exemplary embodiment are dealt with as the majority of both characteristics are again identical.

The male centering elements 120D in this exemplary embodiment are constructed from three sections, a cylindrical base 120D1, a truncated conical middle section 120D2 and again a cylindrical tip 120D3. The female centering elements 220D have a corresponding negative shape whereby again a narrow gap S is formed between the two centering elements 120D, 220D. This type of centering element 120D, 220D is advantageous as there can initially be a relatively large clearance between the container lid 200 and the container trough 100 when placing container lid 200 on container trough 100, as the tip 120D3 of the male centering element 120D must initially be introduced into the female centering element 220D. As the placing of the container lid 200 on to container trough 100 progresses the inclined surface of the middle section 120D2 comes into contact with the boundary of the female centering element 220D and ensures a self-centering of the container lid 200 in relation to the container trough 100 by the fact that the border of the female centering element 220D slides along the oblique surface of the middle section 120D2 of the male centering element 120D until the base 120D1 can also be introduced into the female centering element 220D.

Furthermore, the male and female centering elements should be dimensioned such that the fastening elements 210 can only be introduced into the locking mounts 110 if the container lid is completely centered in relation to the container trough, i.e. the male centering elements are completely accommodated in the female centering elements.

According to a further exemplary embodiment, the centering elements are provided inside the inside of the container In this way centering surfaces are provided in the corner areas of the container trough which run inwards from the upper edge 101 of the container trough 100 towards its floor. These centering surfaces then correspond to the female centering elements along which, for example, bar-shaped centering elements, which are provided inside the seal 201 on the inside of the container lid 200 in the corner areas of the container lid 200, slide whilst the container lid 200 is being placed on the container trough 100. The bar-shaped centering elements then correspond to the male centering elements.

In all exemplary embodiments, the centering elements provided on the container trough can be formed directly with the container trough or they can be arranged on front panels or on other panels or on other components which are provided on the container trough. The centering elements need not be arranged in pairs It is also possible to provide an odd number of one type of centering element whereby then a corresponding number of the other type of centering elements is provided. It is also possible for overall more female than male centering elements to be provided so that some female centering elements are only used in, for example, one or few of several positions of the container lid relative to the container trough. For example, with a square container 1 it is possible for two fastener straps 230 to be provided which are arranged opposite to each other on the container lid 200, whereby a male centering element 120, 120A, 120B, 120C, 120D is provided to the right and left of every fastener strap 230. Two front panels 110 and two lateral panels are provided on the container trough 100 which all have a locking mount 130 and whereby a female centering element 220, 220A, 220B, 220C, 220D is provided to the right and left of every locking mount 130. The container lid 200 is then still always able to be placed in four positions on the container trough 100, however, only half of the female centering elements accommodate their male counterparts.

The person skilled in the art can ascertain these and other advantages by studying the application documents. Many characteristics which are described here in relation to the individual exemplary embodiments, can also be realized in combination with other exemplary embodiments, so, for example, the male centering elements 120 can also be provided on the container lid and the corresponding female centering elements 220 can be provided on the container trough 100. Equally, the materials specified can be used for all exemplary embodiments. The centering elements can be made from metal or plastic or both. If the centering elements are made from plastic, it is particularly advantageous for them to have a U-shaped axial cross section, as centering elements, which have fundamentally the same wall thickness throughout, can be produced in this way. A uniform wall thickness is advantageous in so far as no uneven surfaces occur during the cool-down phase in an injection molding process which often occur if a component is designed with strongly differing wall thicknesses. Advantageously, the centering elements for this from the side which is averted from the front face, i.e. from the side which is not directly visible to the user, are designed with recesses Overall, all characteristics of the individual exemplary embodiments can be combined in any way appropriate.

The invention claimed is:
1. A container having
a container trough with an access opening,
a container lid, and
a seal which is arranged between the container trough and the container lid in the closed state of the container, whereby the seal, in the closed state of the container, is in contact with the container trough and the container lid along the entire periphery of the access opening, and a centering aid
wherein
the centering aid has a first centering device, which is provided on either the container lid or the container trough,
a second centering device which is provided on the other one of either the container lid or the container trough,
the centering devices are made from a material which has a higher modulus of elasticity than the seal,
the container trough includes a first fastening element adjacent to the first centering device, and
the container lid includes a second fastening element pivotally connected to the container lid adjacent to the second centering device, and the container lid is secured to the container trough when the second fastening element is fastened to the first fastening element, wherein
the first centering device has four planar projections which run in a lateral direction to form an angle in relation to the longitudinal axis of the container and the transverse axis of the container and wherein the second centering device has four recesses which are adjusted appropriately to accommodate and interlock corresponding planar projections.

2. A container according to claim 1, wherein
in the closed state of the container the clearance between the first and the second centering device is smaller than the clearance between the container lid and the container trough in the event that no centering devices are provided.

3. A container according to claim 1, wherein
the first centering device has a plurality of male centering elements and
the second centering device has a number of female centering elements.

4. A container according to claim 3, wherein
at least one of the male centering elements is one of a parallelepiped, a cuboid, a pyramid, a truncated pyramid, a cone, a truncated cone and a partial ellipsoid in shape, and
the associated female centering element has a corresponding negative shape.

5. A container according to claim 3, wherein
at least one male centering element and/or a female centering element has an at least partial conical area so that the clearance between the male and the female centering element at the beginning of the movement to place the container lid is greater than in the closed state of the container, wherein the associated female centering element and/or male centering element has a corresponding negative and/or positive shape.

6. A container according to claim 3, wherein
the first centering device comprises an even number of male centering elements which are arranged in the corners of the container lid and/or in the middle of each side of the container lid.

7. A container according to claim 1, wherein
the first and second centering devices each have at least one male and one female centering element.

8. A container according to claim 1, wherein
the centering devices are arranged such that, in the closed state of the container, they are arranged outside the interior of the container.

9. A container according to claim 8, wherein
the first centering device is provided directly, or via a front panel arranged on the external front faces of the container trough, on the external front faces,
the container lid includes a pair of second fastening elements which are provided on respective opposite sides of the container lid.

10. A container according to claim 1, wherein
the projections are provided on both sides of a fastening mount on the top of two front panels which are arranged on both outer front faces of the container trough, wherein
the planar projections are more strongly beveled on their lateral front face than on their central front face so that the projections fundamentally taper in a distal direction externally, wherein
two recesses are each formed in a component which is provided between the internal front face of the container lid and the seal.

11. A container according to claim 1, wherein
the first centering device is provided on the inside of the container lid inside the seal and the second centering device is provided on the container trough.

12. A container according to claim 1, wherein
the centering aid has a symmetrical construction with an angle of rotation of 360°/n, whereby n is a positive integer such that the container lid is sealingly connected to the container trough in each of n rotational orientations of the container lid relative to the container trough.

13. The container according to claim 1, wherein the centering devices are made from at least one of a rigid plastic and a metal.

14. The container according to claim 1, wherein the first centering device includes a surface that extends in a direction that intersects an axis of the container trough.

15. The container according to claim 1, wherein
the first centering device includes a first male centering element and a second male centering element, the first male centering element has a first surface that extends in a first direction that intersects an axis of the container trough, and the second male centering element has a second surface that extends in a second direction that intersects each of the first direction and the axis of the container trough.

* * * * *